Figure 1:
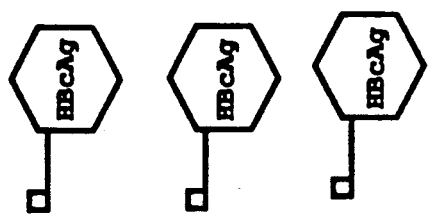
Figure 1:
Figure 1:
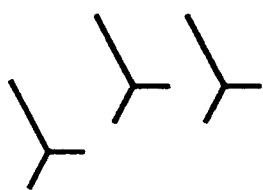
Figure 1:
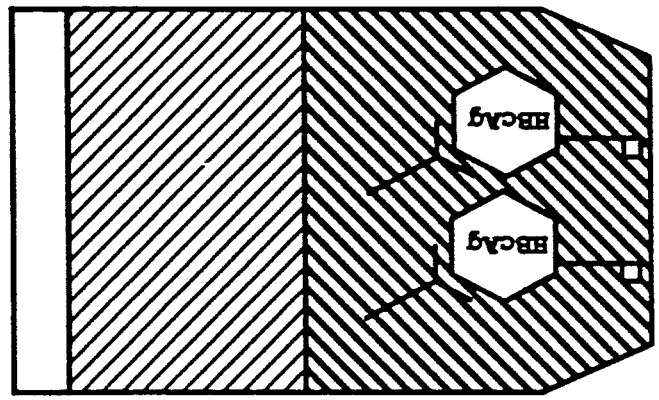

United States Patent [19]

Donovan et al.

[11] Patent Number: 5,141,848

[45] Date of Patent: Aug. 25, 1992

[54] CONFIRMATORY IMMUNOASSAY USING MICROPARTICLE SEPARATION

[75] Inventors: James J. Donovan, Waukegan; Robin M. Pennington, Evanston; Jonathan Staller, McHenry, all of Ill.

[73] Assignee: Abbott Laboratories, Abbott Park, Ill.

[21] Appl. No.: 511,863

[22] Filed: Apr. 10, 1990

Related U.S. Application Data

[63] Continuation of Ser. No. 314,669, Feb. 21, 1989, abandoned, which is a continuation of Ser. No. 6,419, Jan. 21, 1987, abandoned.

[51] Int. Cl.⁵ .................. G01N 33/576; G01N 33/543
[52] U.S. Cl. ......................................... 435/5; 435/962; 435/967; 436/518; 436/533; 436/534; 436/820; 436/825
[58] Field of Search ................ 435/7.1, 7.92, 235.1, 435/34, 5; 436/501, 518, 533, 534, 536, 540, 541, 820, 823, 824, 825

[56] References Cited

U.S. PATENT DOCUMENTS

| Re. 29,474 | 11/1977 | Axen et al. | 424/1 |
|---|---|---|---|
| 4,278,651 | 7/1981 | Hales | 424/1 |
| 4,617,260 | 10/1986 | McAleer et al. | 435/5 |
| 4,661,445 | 4/1987 | Saxinger et al. | 435/7 |
| 4,690,906 | 9/1987 | Duheille et al. | 436/512 |

Primary Examiner—Esther L. Kepplinger
Assistant Examiner—Donna C. Wortman
Attorney, Agent, or Firm—Daniel R. Curry

[57] ABSTRACT

The invention relates to assays utilizing microparticle separation. More particularly, the invention relates to microparticle assays used for confirmation of ligands in a biological sample.

8 Claims, 1 Drawing Sheet

CONFIRMATORY IMMUNOASSAY USING MICROPARTICLE SEPARATION

This is a continuation of U.S. application Ser. No. 314,669, filed Feb. 21, 1989, now abandoned, which is a continuation of U.S. application Ser. No. 006,419, filed Jan. 21, 1987, now abandoned.

BACKGROUND OF THE INVENTION

The invention relates to assays used to confirm various ligands in a biological sample. The invention further relates to a microparticle neutralization assay which can be used to confirm ligands in a biological sample.

Several types of diagnostic assays for detecting or confirming ligands in a sample are currently available. An example of such assays includes direct sandwich immunoassays wherein a ligand-specific binding substance such as an antigen or antibody is coated on a solid phase and contacted with a biological sample thought to contain a ligand of interest. Next, the solid phase is contacted with a ligand-specific binding substance labeled with an appropriate label such as an enzyme, fluorescent label or radioisotope. The label can then be detected to determine the presence or quantity of ligand present in the sample. An example of a direct sandwich assay is Auszyme® immunoassay for detection of hepatitis B surface antigen available from Abbott Laboratories, Abbott Park, Ill.

Another example of an assay is a competitive or inhibition immunoassay wherein a ligand is detected in a biological sample by measuring the ligand's ability to compete with or inhibit binding of a ligand reagent for ligand-specific binding sites on a solid phase or labeled reagent. An example of a competitive immunoassay is Corab® immunoassay for antibody to hepatitis B core antigen also available from Abbott Laboratories.

Still another example of an assay for detecting ligands in a sample is the Western Blot procedure described by Towbin and Gordon, *J. Immun. Meth.*, 72:313-340, 1984. This procedure involves electrophoresis of a known ligand-specific binding substance such as an antigen or antibody on sodium-dodecyl-sulfate polyacrylamide gels (SDS-PAGE). The ligand-specific binding molecule generates a characteristic banding pattern on the gel. This banding pattern is transferred under an electric current from the SDS-PAGE to nitrocellulose filter paper. The filter paper is then incubated with a biological sample containing a ligand of interest. Any ligand in the sample specific for the known ligand-specific binding substance binds to the nitrocellulose filter paper to form a complex such as an antigen-antibody complex. The antigen-antibody complex with its characteristic banding pattern is visualized using a labeled ligand-specific binding substance against the antigen-antibody complex. The Western Blot procedure is a very time-consuming and technique-sensitive procedure involving expensive equipment and highly trained personnel. Therefore, this procedure is not feasible for many laboratories.

Yet another type of assay is a neutralization procedure for confirming samples thought to be positive for a ligand of interest. A ligand-specific binding substance, usually an antibody or antigen, is used as a neutralizing reagent and is added to the biological sample which has previously been tested as positive by another assay method. In a truly positive sample, the neutralization reagent binds to the ligand of interest and prevents it from reacting with any other reagents. The biological sample containing the neutralization reagent is then assayed in an immunoassay such as those described above. A reduction in the ligand previously detected indicates the sample was neutralized and is a true positive. This neutralization procedure works well for confirming certain assays, for example, hepatitis B surface antigen assays such as Auszyme® II confirmatory neutralization assay, Abbott Laboratories. However, one problem with such assays is that the neutralization reagent can react nonspecifically with the solid phase of the immunoassay yielding equivocal results.

DEFINITIONS

The term "ligand" as used in the present invention refers to antigens, antibodies, haptens, hormones and their receptors, DNA, RNA and other organic substances for which a specific-binding substance can be provided. Representative ligands which can be determined by methods of the present invention are viral, bacterial, fungal, rickettsial, and tumor-associated antigens and their corresponding antibodies and DNA or RNA.

The term "biological sample" as used herein refers to biological fluids including human biological fluids such as human serum, plasma, saliva, urine or tissue culture fluids.

The term "reagent(s)" as used herein refers to any of the components to be added in the steps of an immunoassay. Such reagents include, for example, a neutralizing reagent.

The term "assay" as used in the present invention refers to any test system used to detect a ligand.

SUMMARY OF THE INVENTION

The invention is an assay for confirming ligands in biological samples utilizing neutralizing microparticles. According to the invention, a ligand-specific binding substance is attached, covalently or noncovalently, to microparticles such as latex, plastic, magnetic or polymeric materials of about 0.1 to 10 microns in size or other microscopic particles which are well known to those skilled in the art (neutralizing microparticles). The neutralizing microparticles are incubated with a biological sample found previously to be positive for a ligand of interest in an assay (original assay). The ligand, if truly present in the sample, binds to the neutralizing microparticles. The neutralizing microparticles with the bound ligand are then removed from the sample by methods such as centrifugation, gravity, magnetic field or filtration. The sample is then retested in the original assay and should now test negative since the ligand, if present, has been removed by the neutralizing microparticles.

The inventive assay utilizing microparticles is especially useful for confirming the presence of antibodies to hepatitis B core antigen (anti-HBc) in a biological sample. The neutralizing assay utilizing microparticles can be applied to assays for the detection of many other ligands.

The following example is intended to illustrate the invention and not to limit its scope or spirit.

EXAMPLE

This example demonstrates a neutralizing assay for confirming the presence of anti-HBc. The assay comprises first coating microparticles with hepatitis B core antigen (the "neutralizing reagent"). Preferably the core antigen used to coat the microparticles is different from or from a different source than the hepatitis B core antigen used in the original assay. For example, if the original assay utilizes a solid phase containing hepatitis B core antigen derived by recombinant DNA methods, then it is preferable to use native hepatitis B core antigen derived from a human source for coating the microparticles in the neutralization assay. The neutralizing reagent is incubated with a biological sample shown to be positive for anti-HBc in an immunoassay such as Corzyme® or Corab® immunoassays available from Abbott Laboratories, Abbott Park, Ill. After incubating from 1 to 24 hours at 4 to 50 degrees Celsius, the neutralizing reagent with bound anti-HBc is removed from the sample by centrifugation. The sample is then retested in the original anti-HBc immunoassay. A negative result in the retesting of the sample confirms the positive result of the original assay.

Two reagents are required for the above-described neutralizing assay for anti-HBc: 1) The neutralizing reagent: microparticles coated with hepatitis B core antigen and 2) microparticles coated with a protein other than hepatitis B core antigen to act as a control (control microparticles). Examples of these proteins are bovine serum albumin (BSA), ovalbumin, *E. coli* proteins etc. Preparation of the two coated microparticles is outlined below.

1. Ion Exchange of Microparticles

Polystyrene carboxylated microparticles (0.498 microns, Seragen, Indianapolis, Ind.) are diluted to 10% solids with distilled water. The 10% solid solution (15 ml) is combined with 9.0 grams AG 501-X8 ion exchange resin (Bio-Rad Laboratory, Richmond, Calif.). The solution is placed on a shaker or end-over-end rotator for 2 hours at room temperature. The microparticles are separated from the resin by aspiration of the solution through a coarse grind scintered glass funnel. The filtrate containing the microparticles is saved, and the resin is washed with distilled water until the filtrate is clear, saving all washes. The filtrates are combined and centrifuged at 400×g for 30 minutes to pellet all of the microparticles. The supernatant is gently removed and discarded. The pellet is resuspended in distilled water to a final volume of 60 ml which is equivalent to 2.5% solids.

2. Coating of Microparticles with Protein

Ion-exchanged microparticles described above (2.5 ml) are combined with 2.5 ml EDAC [1-ethyl-3-(3-dimethylaminopropyl carbodiimide)] (0.2 mg/ml in distilled water), 17.5 ml of 15 mM MES [2(n-morpholino)ethanesulfonic acid], pH 4.75 and 2.5 ml of a protein solution (hepatitis B core antigen or *E. coli* protein for control microparticles). The microparticle solution is placed on an end-over-end rotator for 1 hour at 45 degrees Celsius. After incubation, the coated microparticles are centrifuged at 4000×g for 30 minutes. The supernatant is removed. The pelleted microparticles are washed by resuspending the microparticles in 25.0 ml of phosphate-buffered saline, pH 7.2 and 0.1% Tween® 20 and centrifuged as above. The supernatant is removed and the washing procedure is repeated two additional times. After the third centrifugation, the microparticle pellet is resuspended in 2.0 ml of 50 mM Tris® buffer, 150 mM NaCl, pH 8.0 and a preservative and stored at 2-8 degrees Celsius.

3. Anti-HBc Neutralization Assay Protocol

The protocol for an anti-HBc neutralization assay is diagrammed in FIG. 1. A human serum or plasma sample (0.25 ml) which had been found to be positive in an anti-HBc assay is incubated for 2 hours with 10 ul of the neutralizing reagent described above. Another aliquot of the sample (0.25 ml) is incubated for 2 hours with 10 ul of control microparticles. The incubations are performed at room temperature. At the end of the incubation period the samples are centrifuged at high speed, for example, 10,000×g for 3 minutes to remove neutralizing microparticles from the sample. The supernatant sample is then removed and reassayed in the original anti-HBc assay. A significant neutralization of anti-HBc (i.e., greater than 20%) indicates a confirmation of true anti-HBc reactivity. No neutralization indicates either that the sample is a false positive or that an error occurred in the original assay.

A possible calculation for determining neutralization using an anti-HBc assay (Corzyme® immunoassay, Abbott Laboratories, Abbott Park, Ill.) is illustrated in Table I. Those samples exhibiting a percent neutralization greater than 20% are considered positive. Samples with a percent neutralization less than 20% are considered negative. Table II indicates the results when testing a group of anti-HBc negative and positive specimens. All samples that were positive in the anti-HBc assay (Corzyme® immunoassay) were neutralized in the anti-HBc neutralization assay. Specimens showing no reaction in the anti-HBc were negative in the anti-HBc neutralization assay.

TABLE I

CALCULATION FOR PERCENT NEUTRALIZATION $$\frac{A492 \text{ NEUTRALIZING REAGENT} - A492 \text{ CONTROL MICROPARTICLES}}{A492 \text{ NEGATIVE CONTROL}} \times 100$$

A492 = Absorbance at 492 nm

TABLE II

ANTI-HBc NEUTRALIZATION: POPULATION STUDIES

| Sample Type | Corzyme | | Neutral Assay | |
| --- | --- | --- | --- | --- |
| (Number) | Positive | Negative | Positive* | Negative |
| Anti-HBc Negative (48) | 1 | 47 | 1 | 47 |
| Anti-HBc Positive (33) | 32 | 1 | 32 | 1 |

*Percent neutralization greater tan 20%

There are many advantages to the microparticle neutralization assay. First, coating the microparticles with binding substance facilitates removal of the neutralizing reagent from a sample and improves specificity. If ligand-specific binding substance is not removed, as in the prior art confirmatory neutralization assays, it may bind to the solid phase upon retesting. This causes equivocal results in some assays such as Corzyme® immunoassay for anti-HBc. Second, microparticles are easy to handle. They can be removed from solution with a short centrifugation. Third, the neutralization assay can be performed at room temperature, elevated temperatures or at refrigerated temperatures. Fourth, the neutralization assay confirms positive samples conclusively.

Although this invention has been described with respect to specific modifications, the details thereof are not to be construed as limitations, for it will be apparent that various equivalents, changes and modifications may be utilized without departing from the spirit and scope of the invention; therefore, it is understood that such equivalents are intended to be included herein.

An example of a microparticle neutralization assay is described. The anti-HBc neutralization assay is designed to work in conjunction with any anti-HBc assay including Corzyme® and Corab® immunoassays. The assay is described as follows:

a. Samples previously positive in an anti-HBc assay are incubated with hepatitis B core antigen (HBcAg) coated microparticles. If there is any anti-HBc present in the sample, it will bind to the neutralizing microparticles.

b. The neutralizing microparticles are centrifuged to remove them from solution.

c. The supernatant is assayed in any anti-HBc assay.

The assay control utilizes bovine serum albumin (BSA) coated microparticles in place of the neutralizing microparticles.

What is claimed is:

1. An assay for confirming the presence of a ligand in a biological sample, the sample having been tested previously utilizing a binding substance specific for the ligand and found positive for the ligand, the assay comprising:
   a) contacting the sample with microparticles which have been coated with a binding substance specific for the ligand for a time and under conditions sufficient for the ligand to bind to said microparticles
   b) removing said microparticles which have been coated with a binding substance specific for the ligand from said sample thereby forming a supernatant sample; and
   c) retesting said supernatant sample for presence of the ligand to determine if ligand has been removed with the removal of the microparticles, wherein a negative result upon retesting confirms the previous positive assay result.

2. The assay of claim 1 wherein the ligand is antibody to hepatitis B core antigen.

3. The assay of claim 1 wherein said microparticles are removed by centrifugation.

4. The assay of claim 1 wherein the binding substance on the microparticles is different than the binding substance used in the previous test.

5. The assay of claim 1 wherein the biological sample is assayed with control microparticles along with the microparticles which have been coated with a binding substance specific for the ligand.

6. An assay for confirming the presence of antibodies to hepatitis B core antigen in a biological sample, the sample having been previously tested and found positive for anti-HBc antibody utilizing a binding substance specific for anti-HBc antibody, the assay comprising:
   a) contacting the sample with microparticles which have been coated with hepatitis B core antigen for a time and under conditions sufficient for anti-HBc antibody to bind to said microparticles;
   b) removing said microparticles which have been coated with hepatitis B core antigen from said sample thereby forming a supernatant sample; and
   c) retesting said supernatant sample for presence of anti-HBc antibody to determine if anti-HBc antibody has been removed with the removal of the microparticles, wherein a negative result upon retesting confirms the previous positive assay result.

7. The neutralizing assay of claim 6 wherein the microparticles are removed by centrifugation.

8. The assay of claim 6 wherein the hepatitis B core antigen on the microparticles is different than the binding substance for anti-HBc in the previous test.

* * * * *